United States Patent [19]

Derouane et al.

[11] Patent Number: 4,647,442

[45] Date of Patent: Mar. 3, 1987

[54] CRYSTALLINE SILICOPHOSPHOALUMINATE FROM A TWO PHASE MEDIUM

[75] Inventors: Eric G. Derouane, Hopewell; Roland von Ballmoos, Pennington, both of N.J.

[73] Assignee: Mobil Oil Corporation, New York, N.Y.

[21] Appl. No.: 642,966

[22] Filed: Aug. 21, 1984

Related U.S. Application Data

[63] Continuation-in-part of Ser. No. 562,778, Dec. 19, 1983, abandoned.

[51] Int. Cl.[4] .................... C01B 15/16; C01B 33/28
[52] U.S. Cl. ................... 423/306; 423/305; 423/328; 423/329; 502/214
[58] Field of Search ................. 423/328, 329, 329 T, 423/338, 305, 306; 502/233, 263, 214

[56] References Cited

U.S. PATENT DOCUMENTS

| | | | |
|---|---|---|---|
| 3,697,550 | 10/1972 | Bayne et al. | 260/346 |
| 3,801,704 | 4/1974 | Kobayashi et al. | 423/309 |
| 3,904,550 | 9/1975 | Pine | 502/439 |
| 4,014,945 | 3/1977 | Zimmerschied et al. | 260/635 |
| 4,071,471 | 1/1978 | Banks et al. | 502/174 |
| 4,158,621 | 6/1979 | Swift et al. | 208/114 |
| 4,179,358 | 12/1979 | Swift et al. | 208/114 |
| 4,210,560 | 7/1980 | Kehl | 502/208 |
| 4,222,896 | 9/1980 | Swift et al. | 502/65 |
| 4,228,036 | 10/1980 | Swift et al. | 502/65 |
| 4,301,034 | 11/1981 | McDaniel | 423/338 |
| 4,310,440 | 1/1982 | Wilson et al. | |
| 4,361,705 | 11/1982 | Marcelin et al. | 568/462 |
| 4,365,095 | 12/1982 | Marcelin et al. | 568/462 |
| 4,385,994 | 5/1983 | Wilson et al. | 210/689 |
| 4,440,871 | 4/1984 | Lok et al. | 502/214 |
| 4,526,767 | 7/1985 | Robinson et al. | 423/329 T |

FOREIGN PATENT DOCUMENTS 1018264 1/1966 United Kingdom ............ 423/328 C

OTHER PUBLICATIONS

Lok et al., "Zeolites" 1983, vol. 3, Oct. pp. 282–291.

*Primary Examiner*—John Doll
*Assistant Examiner*—Lance Johnson
*Attorney, Agent, or Firm*—Alexander J. McKillop; Michael G. Gilman; Edward F. Kenehan, Jr.

[57] ABSTRACT

An improved method of synthesis for a composition comprising crystalline silicophosphoaluminate (MCM-2) is provided. The composition has ion-exchange properties and is readily convertible to catalytically active material. The synthesis method requires two liquid phases comprising a suitable organic or inorganic directing agent and specific reactants, including a specific aluminum phosphate of the ALPO-5 structure.

2 Claims, No Drawings

CRYSTALLINE SILICOPHOSPHOALUMINATE FROM A TWO PHASE MEDIUM

CROSS REFERENCE TO RELATED APPLICATION

This application is a continuation-in-part of co-pending U.S. application Ser. No. 562,778, filed Dec. 19, 1983, now abandoned the entire disclosure of which is expressly incorporated herein by reference.

BACKGROUND

This invention relates to a novel synthetic crystalline silicophosphoaluminate molecular sieve material, designated "MCM-2", containing aluminum, silicon and phosphorus in its framework, to a method for its synthesis and to use thereof in catalytic conversion of organic compounds. The crystalline material of this invention exhibits ion-exchange properties and can easily be converted to catalytically active material.

Zeolitic materials, both natural and synthetic, have been demonstrated in the past to have catalytic properties for various types of hydrocarbon conversion. Certain zeolitic materials are ordered, porous crystalline aluminosilicates having a definite crystalline structure as determined by X-ray diffraction, within which there are a large number of smaller cavities which may be interconnected by a number of still smaller channels or pores. These cavities and pores are uniform in size within a specific zeolitic material. Since the dimensions of these pores are such as to accept for adsorption molecules of certain dimensions while rejecting those of larger dimensions, these materials have come to be known as "molecular sieves" and are utilized in a variety of ways to take advantage of these properties.

Such molecular sieves, both natural and synthetic, include a wide variety of positive ion-containing crystalline aluminosilicates. These aluminosilicates can be described as rigid three-dimensional frameworks of $SiO_4$ and $AlO_4$ in which the tetrahedra are cross-linked by the sharing of oxygen atoms whereby the ratio of the total aluminum and silicon atoms to oxygen atoms is 1:2. The electrovalence of the tetrahedra containing aluminum is balanced by the inclusion in the crystal of a cation, for example an alkali metal or an alkaline earth metal cation. This can be expressed wherein the ratio of aluminum to the number of various cations, such as Ca/2, Sr/2, Na, K or Li, is equal to unity. One type of cation may be exchanged either entirely or partially with another type of cation utilizing ion exchange techniques in a conventional manner. By means of such cation exchange, it has been possible to vary the properties of a given aluminosilicate by suitable selection of the cation. The spaces between the tetrahedra are occupied by molecules of water prior to dehydration.

Prior art techniques have resulted in the formation of a great variety of synthetic zeolites. The zeolites have come to be designated by letter or other convenient symbols, as illustrated by zeolite A (U.S. Pat. No. 2,882,243), zeolite X (U.S. Pat. No. 2,882,244), zeolite Y (U.S. Pat. No. 3,130,007), zeolite ZK-5 (U.S. Pat. No. 3,247,195), zeolite ZK-4 (U.S. Pat. No. 3,314,752), zeolite ZSM-5 (U.S. Pat. No. 3,702,886), zeolite ZSM-11 (U.S. Pat. No. 3,709,979), zeolite ZSM-12 (U.S. Pat. No. 3,832,449), zeolite ZSM-20 (U.S. Pat. No. 3,972,983), zeolite ZSM-35 (U.S. Pat. No. 4,016,245), zeolite ZSM-38 (U.S. Pat. No. 4,046,859). and zeolite ZSM-23 (U.S. Pat. No. 4,076,842) merely to name a few.

The crystalline silicophosphoaluminate of the present invention is not an aluminosilicate zeolite, but it is a crystalline material with an ordered pore structure which exhibits ion-exchange ability.

Aluminum phosphates are taught in U.S. Pat. Nos. 4,310,440 and 4,385,994, for example. Aluminum phosphate materials have electroneutral lattices and, therefore, are not useful as ion-exchangers or as catalyst components. U.S. Pat. No. 3,801,704 teaches an aluminum phosphate treated in a certain way to impart acidity.

The phosphorus-substituted zeolites of Canadian Pat. Nos. 911,416; 911,417 and 911,418 are referred to as "aluminosilicophosphate" zeolites. Some of the phosphorus therein appears to be occluded, not structural.

U.S. Pat. No. 4,363,748 describes a combination of silica and aluminum-calcium-cerium phosphate as a low acid activity catalyst for oxidative dehydrogenation. Great Britain Pat. No. 2,068,253 discloses a combination of silica and aluminum-calcium-tungsten phosphate as a low acid activity catalyst for oxidative dehydrogenation. U.S. Pat. No. 4,228,036 teaches an alumina-aluminum phosphate-silica matrix as an amorphous body to be mixed with zeolite for use as cracking catalyst. U.S. Pat. No. 3,213,035 teaches improving hardness of aluminosilicate catalysts by treatment with phosphoric acid. The catalysts are amorphous.

U.S. Pat. No. 2,876,266 describes an active silicophosphoric acid or salt phase of an amorphous material prepared by absorption of phosphoric acid by pre-molded silicates or aluminosilicates.

Aluminum phosphates are well known in the art as exemplified by U.S. Pat. Nos. 4,365,095; 4,361,705; 4,222,896; 4,210,560; 4,179,358; 4,158,621; 4,071,471; 4,014,945; 3,904,550 and 3,697,550. Since their neutral framework structure is void of ion-exchange properties, they are used as catalyst supports or matrices. U.S. Pat. No. 4,440,871 describes various crystalline microporous materials characterized as "silicoaluminophosphates." These materials are prepared hydrothermally from aqueous gels containing reactive phosphorus, silicon and aluminum compounds and organic templating agents. The crystalline silicophosphoaluminate synthesized hereby is a molecular sieve exhibiting ion-exchange properties and is easily and conveniently converted to material having intrinsic catalytic activity. Techniques for synthesis of aluminophosphates taught in the art are not useful for synthesis of this crystalline silicophosphoaluminate.

SUMMARY

The present invention is directed to a novel synthetic crystalline silicophosphoaluminate molecular sieve material, hereinafter designated "MCM-2", containing aluminum, silicon and phosphorus in its framework, to a method for its synthesis and to its use as a catalyst component in catalytic conversion of organic, e.g hydrocarbon, compounds.

The anhydrous crystalline MCM-2 has the general formula:

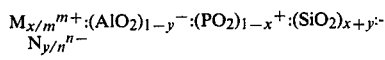

wherein M is a cation of valence m, N is an anion of valence n, and x and y are numbers of from greater than −1 to less than +1 which satisfy the relationships:
 (1) if x is 0, then y is not 0,
 (2) if y is 0, then x is not 0,
 (3) if the atomic ratio of Al/P is greater than 1, then (x+y) is greater than 0.001 and y+0.6x is less than 0.4, and
 (4) if the atomic ratio of Al/P is less than 1, then (x+y) is greater than 0.001 and x+0.5y is less than 0.5.

In the composition above, when x is greater than y the silicophosphoaluminate is a cation exchanger with potential use as an acidic catalyst. When x is less than y, the silicophosphoaluminate is an anion exchanger with potential use as a basic catalyst.

In the synthesized form of the MCM-2, the silicophosphoaluminate can also contain occluded organic material, A, and water molecules entrapped during the synthesis and filling the microporous voids. It then has the general formula:

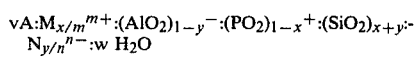

$$vA:M_{x/m}{}^{m+}:(AlO_2)_{1-y}{}^-:(PO_2)_{1-x}{}^+:(SiO_2)_{x+y}:N_{y/n}{}^{n-}:w\, H_2O$$

wherein v is the number of moles of A, occluded organic material resulting from organic directing agent and/or solvent used in synthesis of and filling microporous voids of the MCM-2, which material may be removed upon calcination, w is moles of $H_2O$, e.g. from 0 to about 5, and x and y are the numbers defined above.

The crystalline silicophosphoaluminate of this invention is a unique composition of matter which exhibits a valuable combination of catalytic, sorption and ion-exchange properties which distinguishes it from known aluminum phosphates.

EMBODIMENTS

The silicophosphoaluminate material of the present invention will exhibit unique and useful catalytic, sorptive and shape selective properties along with a silicon/(aluminum+phosphorus) atomic ratio of less than unity, e.g. from about 0.001 to about 0.99. If synthesized with an aluminum/phosphorus atomic ratio of greater than one, the crystalline silicophosphoaluminate exhibits an aluminum/silicon atomic ratio of greater than 1.5, and usually in the range from 1.6 to 600. When the aluminum/phosphorus atomic ratio is of less than one, it exhibits a phosphorus/silicon atomic ratio of greater than unity, usually within the range from 1.2 to 600. It is well recognized that aluminum phosphates exhibit a phosphorus/aluminum atomic ratio of only 0.8 to 1.2 and contain no silicon. Also, the phosphorus-substituted zeolite compositions, sometimes referred to as "aluminosilicophosphate zeolites", have a silicon/aluminum atomic ratio of from 0.66 to 8.0, and a phosphorus/aluminum atomic ratio of from greater than 0 to 1.

The original cations of the as synthesized MCM-2 can be replaced in accordance with techniques well known in the art, at least in part, by ion exchange with other cations. Preferred replacing cations include metal ions, hydrogen ions, hydrogen precursor, e.g., ammonium, ions and mixtures thereof. Particularly preferred cations are those which render the MCM-2 catalytically active, especially for hydrocarbon conversion. These include hydrogen, rare earth metal and metals of Groups IA, IIA, IIIA, IVA, IB, IIB, IIIB, IVB and VIII of the Periodic Table of the Elements.

A typical ion exchange technique would be to contact the synthetic MCM-2 with a salt of the desired replacing cation or cations. Examples of such salts include the halides, e.g. chlorides, nitrates and sulfates.

The framework topology of the MCM-2 containing silicon, phosphorus and aluminum in tetrahedrally coordinated structural positions is similar to that of chabazite, a naturally occurring zeolite.

Crystalline MCM-2 materials of the present invention have substantial ion exchange capacity and catalytic activity. To the contrary, corresponding materials of the same crystalline structure containing only aluminum, phosphorus and oxygen and essentially no silicon in the lattice structures thereof have little or no ion exchange capacity and catalytic activity. Accordingly, for example, the Alpha Value of an MCM-2 material may be at least 100 percent or even at least 1000 percent greater than the Alpha Value of a corresponding material of the same crystalline structure, said corresponding material having only aluminum, phosphorus and oxygen and essentially no silicon in the lattice structure thereof. Such aluminum, phosphorus and oxygen containing materials are generally referred to in the Wilson, et al. U.S. Pat. No. 4,310,440.

The crystalline MCM-2 of the present invention can be beneficially thermally treated, either before or after ion exchange. This thermal treatment is performed by heating the silicophosphoaluminate in an atmosphere such as air, nitrogen, hydrogen, steam, etc., at a temperature of from about 300° C. to about 1100° C., preferably from about 350° C. to about 750° C., for from about 1 minute to about 20 hours. While subatmospheric or superatmospheric pressures may be used for this thermal treatment, atmospheric pressure is desired for reasons of convenience.

MCM-2 exhibits a definite X-ray diffraction pattern which distinguishes it from other crystalline materials. The X-ray diffraction pattren of the as synthesized MCM-2 has the following characteristic values:

TABLE 1-A

| Interplanar d-Spacing (A) | Relative Intensity |
|---|---|
| 9.24 ± 0.1 | vs |
| 6.86 ± 0.1 | m |
| 6.49 ± 0.1 | w |
| 6.25 ± 0.1 | w |
| 5.51 ± 0.05 | s |
| 4.86 ± 0.05 | m |
| 4.30 ± 0.05 | vs |
| 3.51 ± 0.05 | w |
| 3.44 ± 0.05 | w |
| 3.05 ± 0.05 | w |
| 2.92 ± 0.05 | m |
| 2.85 ± 0.02 | m |

Table 1-B lists the characteristic diffraction lines of the calcined (450° C., atmospheric pressure, 4 hours) form of MCM-2.

TABLE 1-B

| Interplanar d-Spacing (A) | Relative Intensity |
|---|---|
| 9.25 ± 0.1 | vs |
| 6.84 ± 0.1 | w |
| 5.51 ± 0.05 | w |
| 4.95 ± 0.05 | w |
| 4.30 ± 0.05 | m |
| 3.43 ± 0.02 | w |
| 2.91 ± 0.02 | w |

TABLE 1-B-continued

| Interplanar d-Spacing (A) | Relative Intensity |
| --- | --- |
| 2.86 ± 0.02 | w |

These X-ray diffraction data were collected with the Rigaku X-ray system, using copper K-alpha radiation. The positions of the peaks, expressed in degrees 2 theta, where theta is the Bragg angle, were determined by step-scanning at 0.02 degrees of 2 theta intervals and a counting time of 1 second for each step. The interplanar spacings, d, measured in Angstrom units (A), and the relative intensities of the lines, $I/I_o$, where $I_o$ is one-hundredth of the intensity of the strongest line, including subtraction of the background, were derived with the use of a profile fitting routine. The relative intensities are given in terms of the symbols vs=very strong (75–100%), s=strong (50–74%), m=medium (25–49%) and w=weak (0–24%). It should be understood that this X-ray diffraction pattern is characteristic of all the species of MCM-2 compositions synthesized by the present invention. Ion exchange of cations with other ions results in a silicophosphoaluminate which reveals substantially the same X-ray diffraction pattern with some minor shifts in interplanar spacing and variation in relative intensity. Other variations can occur, depending on the silicon/aluminum and phosphorus/aluminum ratios of the particular sample, as well as its degree of thermal treatment.

The crystalline MCM-2 material of this invention may be converted to the dry, hydrogen form by the above thermal treatment of the organic cation-containing form or hydrogen ion precursor-containing form resulting from ion exchange.

In general, the silicophosphoaluminate of the present invention can be prepared from a two-phase reaction mixture containing sources of aluminum, phosphorus and silicon and an organic directing agent(s) and an organic solvent. The overall molar composition of the two-phase synthesis mixture is in terms of oxides and organic components:

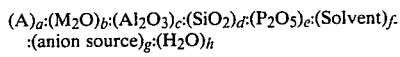
:(anion source)$_g$:(H$_2$O)$_h$ where: $a/(c+d+e)$ is less than 4, $b/(c+d+e)$ is less than 2, $d/(c+e)$ is less than 2, $f/(c+d+e)$ is from 0 to 15, $g/(c+d+e)$ is less than 2 and $h/(c+d+e)$ is from 3 to 150. The "Solvent" is an organic solvent and "A" is any organic compound or material such as that derived from an organic directing agent or organic solvent. The anion is not necessarily separately added to the two-phase system, but may or may not appear in the product crystals from one or more of the other component sources.

Reaction conditions include carefully heating the foregoing reaction mixture at a rate of from 5° C. to 200° C. per hour to a temperature of from about 80° C. to about 300° C. for a period of time of from about 5 hours to about 500 hours until crystals of MCM-2 are formed. A more preferred temperature range is from about 100° C. to about 200° C. with the amount of time at a temperature in such range being from about 24 hours to about 168 hours. During heating and maintaining the reaction mixture at the desired temperature, the pH must be carefully controlled to be from about 2 to about 9. Control of pH can be accomplished by adjusting the concentration of the added organic and/or inorganic base(s).

The reaction is carried out until crystals of the desired MCM-2 form. The crystalline product is recovered by separating same from the reaction medium, as by cooling the whole to room temperature, filtering and washing with water before drying.

The above reaction mixture composition can be prepared utilizing materials which supply the appropriate components. The aqueous phase components may include from the sources of the elements silicon, phosphorus, or aluminum, those not included in the organic phase. The organic phase comprises an organic solvent and a source of at least one of the elements silicon, phosphorus, or aluminum insoluble in the aqueous phase under reaction conditions. The aqueous phase also contains the required organic and/or inorganic directing agent(s).

The useful sources of aluminum, as non-limiting examples, include any known form of aluminum oxide or hydroxide, organic or inorganic salt or compound.

The useful sources of silicon include, as non-limiting examples, any known form of silicon dioxide or silicic acid, alkoxy- or other compounds of silicon.

The useful sources of phosphorus include, as non-limiting examples, any known form of phosphorus acids or phosphorus oxides, phosphates and phosphites, and organic derivatives of phosphorus.

The organic solvent is a $C_5$–$C_{10}$ alcohol or any other liquid compound immiscible with water, as non-limiting examples.

An organic directing agent is selected from the group consisting of organic mono-, di- or polyamines and onium compounds having the following formula:

wherein R or R' is alkyl of from 1 to 20 carbon atoms, heteroalkyl of from 1 to 20 carbon atoms, aryl, heteroaryl, cycloalkyl of from 3 to 6 carbon atoms, cycloheteroalkyl of from 3 to 6 carbon atoms, or combinations thereof; M is a tetracoordinate element (e.g. nitrogen, phosphorus, arsenic, antimony or bismuth) or a heteroatom (e.g. N, O, S, Se, P, As, etc.) in an alicyclic, heteroalicyclic or heteroaromatic structure; and X is an anion (e.g. fluoride, chloride, bromide, iodide, hydroxide, acetate, sulfate, carboxylate, etc.). When M is a heteroatom in an alicyclic, heteroalicyclic or heteroaromatic structure, such structure may be, as non-limiting examples,

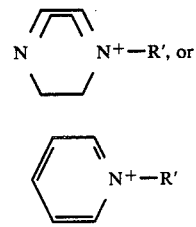

wherein R' is alkyl of from 1 to 20 carbon atoms, heteroalkyl of from 1 to 20 carbon atoms, aryl, heteroaryl, cycloalkyl of from 3 to 6 carbon atoms or cycloheteroalkyl of from 3 to 6 carbon atoms.

Particularly preferred directing agents for the present method include onium compounds, above defined, wherein R is alkyl of 1 to 4 carbon atoms, M is nitrogen and X is halide or hydroxide. Non-limiting examples of these include tetrapropylammonium hydroxide, tetraethylammonium hydroxide and tetrapropylammonium bromide. An inorganic hydroxide or salt of suitable composition can also be used as directing agent, non-limiting examples of which are CsOH and KOH, CsCl and KCl.

A particular method for preparing an MCM-2 material of the present invention comprises the steps of:
(i) preparing a synthesis mixture comprising a liquid organic phase and a liquid aqueous phase, said organic phase comprising an organic solvent and a silicon source soluble in said solvent, said aqueous phase comprising dissolved or partially dissolved AlPO$_4$-5 crystalline aluminum phosphate, said synthesis mixture further comprising a tetraethylammonium directing agent;
(ii) maintaining said reaction mixture under sufficient crystallization conditions until crystals of said MCM-2 are formed; and
(iii) recovering said MCM-2.

The above-mentioned AlPO$_4$-5 material is described in the Wilson et al U.S. Pat. No. 4,310,440, wherein a characteristic X-ray powder diffraction pattern is given for AlPO$_4$-5 therein in Table 2. This Table 2 of the Wilson et al U.S. Pat. No. 4,310,440 is reproduced herein as Table 1-C.

TABLE 1-C

| 2TH | d | 100 × I/Io |
|---|---|---|
| 7.4–7.6 | 11.9–11.6 | 100 |
| 14.8–15.3 | 5.97–5.83 | 13–43 |
| 19.7–20.1 | 4.51–4.42 | 39–92 |
| 20.8–21.2 | 4.27–4.19 | 37–87 |
| 22.3–22.7 | 3.99–3.93 | 62–118 |
| 25.9–26.3 | 3.44–3.39 | 22–35 |

As silicon, aluminum and phosphorus must be available simultaneously to nucleate and crystallize silicophosphoaluminate, the rates of supply of all three elements have to be comparable. This implies that when an aluminum phosphate is used as a source of aluminum and phosphorus, the dissolution of the aluminum phosphate and the hydrolysis of the organic silicon compound should be concerted. Therefore, it may be important to predissolve at least a portion of the aluminum phosphate. Even more critical will be the silicon supply rate which is dependent on factors such as the magnitude of the interface, temperature, pH of the aqueous phase, concentration, and nature of the organic solvent and of the silicon reagent.

Because the hydrolysis and transfer rates of silicon are controlled by the magnitude of the interface, silicon incorporation is expected to be favored as mixing increases.

As mentioned earlier, pH is an important synthesis variable. As the formation of the silicophosphoaluminate proceeds, pH values of around or above neutral (i.e. about 6 or more, up to a maximum of about 9) should be maintained. As the base stability of silicophosphoaluminates is expected to be intermediate between those of aluminum phosphates and zeolites, pH values of about or slightly above 8 are preferred. Because of the major role played by the hydrolysis of the silicon reagent and the necessity to control it in the present method, there is a need to have a nearly constant pH during crystallization. This can be achieved by predissolving the aluminum phosphate before addition of the other reagents.

To achieve and maintain higher pH values (pH=8 or above), even after partial decomposition of the organic hydroxide, inorganic bases may be added. These inorganic bases can also play a role as directing agents.

The MCM-2 crystals prepared by the instant invention can be shaped into a wide variety of particle sizes. Generally speaking, the particles can be in the form of a powder, a granule, or a molded product, such as an extrudate having particle size sufficient to pass through a 2 mesh (Tyler) screen and be retained on a 400 mesh (Tyler) screen. In cases where the catalyst is molded, such as by extrusion, the crystals can be extruded before drying or partially dried and then extruded.

It may be desired to incorporate the new MCM-2 crystal with another material resistant to the temperatures and other conditions employed in various organic conversion processes. Such materials include active and inactive material and synthetic or naturally occurring zeolites as well as inorganic materials such as clays, silica and/or metal oxides, e.g. alumina. The latter may be either naturally occurring or in the form of gelatinous precipitates or gels including mixtures of silica and metal oxides. Use of a material in conjunction with the new MCM-2 crystal, i.e. combined therewith, which is active, tends to alter the conversion and/or selectivity of the overall catalyst in certain organic conversion processes. Inactive materials suitably serve as diluents to control the amount of conversion in a given process so that products can be obtained economically and orderly without employing other means for controlling the rate of reaction. These materials may be incorporated into naturally occurring clays, e.g. bentonite and kaolin, to improve the crush strength of the catalyst under commercial operating conditions. Said materials, i.e. clays, oxides, etc., function as binders for the catalyst. It may be desirable to provide a catalyst having good crush strength because in commercial use it is desirable to prevent the catalyst from breaking down into powder-like materials. These clay binders have been employed normally only for the purpose of improving the crush strength of the overall catalyst.

Naturally occurring clays which can be composited with the new crystal include the montmorillonite and kaolin families which include the subbentonites, and the kaolins commonly known as Dixie, McNamee, Georgia and Florida clays or others in which the main mineral constituent is halloysite, kaolinite, dickite, nacrite, or anauxite. Such clays can be used in the raw state as originally mined or initially subjected to calcination, acid treatment or chemical modification.

In addition to the foregoing materials, the crystalline MCM-2 can be composited with a porous matrix material such as aluminum/phosphate, silica-alumina, silica-magnesia, silica-zirconia, silica-thoria, silica-beryllia, silica-titania as well as ternary compositions such as silica-alumina-thoria, silica-alumina-zirconia silica-alumina-magnesia and silica-magnesia-zirconia. The relative proportions of finely divided crystalline material and inorganic oxide gel matrix vary widely, with the crystal content ranging from about 1 to about 90 percent by weight and more usually, particularly when the composite is prepared in the form of beads, in the range of about 2 to about 80 weight percent of the composite.

The crystalline materials of the present invention are readily convertible to catalytically active material for a variety of organic, e.g. hydrocarbon, compound conversion processes. Such conversion processes include, as non-limiting examples, converting paraffins to aromatics with reaction conditions including a temperature of from about 100° C. to about 700° C., a pressure of from about 0.1 atmosphere to about 60 atmospheres, a weight hourly space velocity of from about 0.5 to about 400 and a hydrogen/hydrocarbon mole ratio of from about 0 to about 20; converting alcohols, e.g. methanol, or ethers, e.g. dimethylether, or mixtures thereof to hydrocarbons including aromatics with reaction conditions including a temperature of from about 275° C. to about 600° C., a pressure of from about 0.5 atmosphere to about 50 atmospheres and a liquid hourly space velocity of from about 0.5 to about 100; and alkylating aromatic hydrocarbons, e.g. benzene and alkylbenzenes, in the presence of an alkylating agent, e.g. olefins, formaldehyde, alkyl halides and alcohols, with reaction conditions including a temperature of from about 340° C. to about 500° C., a pressure of from about atmospheric to about 200 atmospheres, a weight hourly space velocity of from about 2 to about 2000 and an aromatic hydrocarbon/alkylating agent mole ratio of from about 1/1 to about 20/1.

Employing a catalytically active form of the novel MCM-2 material of this invention as a catalyst component, said catalyst possibly containing additional hydrogenation components, reforming stocks can be reformed employing a temperature of from about 370° C. to about 540° C., a pressure of from about 100 psig to about 1000 psig, preferably from about 200 psig to about 700 psig, a liquid hourly space velocity is from about 0.1 to about 10, preferably from about 0.5 to about 4, and a hydrogen to hydrocarbon mole ratio of from about 1 to about 20, preferably from about 4 to about 12.

A catalyst comprising the present MCM-2 molecular sieve can also be used for hydroisomerization of normal paraffins, when provided with a hydrogenation component, e.g. platinum. Such hydroisomerization is carried out at a temperature of from about 90° C. to about 375° C., preferably from about 145° C. to about 290° C., with a liquid hourly space velocity of from about 0.01 to about 2, preferably from about 0.25 to about 0.50, and with a hydrogen to hydrocarbon mole ratio of from about 1:1 to about 5:1. Additionally, such a catalyst can be used for olefin or aromatic isomerization, employing a temperature of from about 200° C. to about 480° C.

Such a catalyst can also be used for reducing the pour point of gas oils. This reaction is carried out at a liquid hourly space velocity of from about 10 to about 30 and at a temperature of from about 425° C. to about 595° C.

Other reactions which can be accomplished employing a catalyst comprising the MCM-2 of this invention containing a metal, e.g. platinum, include hydrogenation-dehydrogenation reactions and desulfurization reactions, olefin polymerization (oligomerization) and other organic compound conversions, such as the conversion of alcohols (e.g. methanol) or ethers (e.g. dimethylether) to hydrocarbons, and the alkylation of aromatics (e.g. benzene) in the presence of an alkylating agent (e.g. ethylene).

In order to more fully illustrate the nature of the invention and the manner of practicing same, the following examples are presented. In the examples, whenever adsorption data are set forth for comparison of sorptive capacities for various adsorbants, they were determined as follows:

A weighed sample of the calcined adsorbant was contacted with a flowing stream of the equilibrium vapor of the adsorbate at 25° C., admixed with dry nitrogen. Adsorbates were water vapor and n-hexane, 2-methylpentane, xylene or cyclohexane vapors. The sample temperature was maintained at 90° C. for adsorbates other than ortho-xylene for which it was 120° C. and water for which it was 60° C. The increase in weight was measured gravimetrically and converted to the adsorption capacity of the sample in weight percent of calcined adsorbant.

When ion-exchange capacity is examined, it is determined by titrating with a solution of sulfamic acid the gaseous ammonia evolved during the temperature programmed decomposition of the ammonium-form of the silicophosphoaluminate. The method is described in *Thermochimica Acta*, Vol. III, pp. 113-124, 1971 by G. T. Kerr and A. W. Chester, incorporated herein by reference as to that description.

EXAMPLE 1

A two-phase synthesis reaction mixture was prepared with the organic phase comprised of 60 g 1-hexanol and 10 g $Si(OC_2H_5)_4$, and the aqueous phase comprised of 23.1 g $H_3PO_4$ (85%), 10 g $Al_2O_3$, 84 g TPAOH (25%) and 30 g $H_2O$. The reaction mixture as a whole had a composition incuding 10.8% Si, 45.0% P and 44.2% Al, the percentages atomic. The directing agent in the organic phase was the TPAOH, i.e. tetrapropylammonium hydroxide.

The reaction mixture was heated at 50° C. per hour to 150° C. and matained at that temperature for 168 hours until crystals of silicophosphoaluminate formed. Starting pH was between 5 and 7.

The crystalline product was separated from the reaction mixture by filtration, water washed and then dried at 80° C. The product crystals were analyzed to contain 17.5% Si, 37.2% P and 45.4% Al, percentages atomic, and to be large in size. A sample of the as synthesized silicophosphoaluminate was then submitted for X-ray analysis and found to be a crystalline molecular sieve exhibiting the diffraction lines shown in Table 2.

TABLE 2

| Interplanar d-Spacing (A) | Observed 2 × Theta | Relative Intensiity, I/Io |
| --- | --- | --- |
| 9.2412 | 9.563 | 99.21 |
| 6.8600 | 12.894 | 24.93 |
| 6.4868 | 13.640 | 7.48 |
| 6.2515 | 14.155 | 14.65 |
| 5.5144 | 16.059 | 72.90 |
| 4.8868 | 18.138 | 21.38 |
| 4.8257 | 18.370 | 11.67 |
| 4.3030 | 20.624 | 100.00 |
| 4.2584 | 20.843 | 23.57 |
| 4.0000 | 22.205 | 5.00 |
| 3.8400 | 23.142 | 5.00 |
| 3.5075 | 25.373 | 21.42 |
| 3.4376 | 25.897 | 22.89 |
| 3.3947 | 26.230 | 7.27 |
| 3.1239 | 28.550 | 1.77 |
| 3.0495 | 29.262 | 14.07 |
| 3.0160 | 29.594 | 5.90 |
| 2.9190 | 30.601 | 33.97 |
| 2.8492 | 31.370 | 25.06 |

EXAMPLE 2

The synthesis of Example 1 was repeated except that the aqueous phase contained 17.0 g $Al_2O_3$. The resulting product crystalline silicophosphoaluminate was of small crystal size with 13.2% Si, 36.3% P and 50.5% Al, percentages atomic.

EXAMPLE 3

A quantity of the crystalline silicophosphoaluminate of Example 1 was calcined at 450° C. in nitrogen for 4 hours and then X-ray analyzed. The results are presented in Table 3.

TABLE 3

| Interplanar d-Spacing (A) | Observed 2 × Theta | Relative Intensity, I/Io |
|---|---|---|
| 9.2476 | 9.556 | 100.00 |
| 6.8414 | 12.929 | 23.34 |
| 6.2800 | 14.090 | 2.00 |
| 5.5050 | 16.087 | 16.61 |
| 4.9465 | 17.918 | 5.05 |
| 4.6200 | 19.194 | 2.00 |
| 4.2923 | 20.676 | 35.99 |
| 3.8415 | 23.134 | 4.72 |
| 3.5423 | 25.119 | 6.97 |
| 3.4266 | 25.982 | 7.73 |
| 3.2100 | 27.768 | 2.00 |
| 3.1600 | 28.216 | 2.00 |
| 2.9086 | 30.174 | 15.30 |
| 2.8621 | 31.226 | 8.93 |

EXAMPLE 4

A two-phase synthesis reaction mixture was prepared with the organic phase comprised of 60 g 1-hexanol and 10 g $Si(OC_2H_5)_4$, and the aqueous phase comprised of 23.1 g $H_3PO_4$ (85%), 10 g $Al_2O_3$, and 71 g $H_2O$. Thirty-seven grams of tetraethylammonium hydroxide (TEAOH, 40%) and 2 ml of $5.10^{-2}$M CsOH were added as directing agents. The reaction mixture as a whole had a composition including 10.8% Si, 45.1% P and 44.1% Al, the percentages atomic.

The reaction mixture was heated at 50° C. per hour to 130° C. and maintained at that temperature for 24 hours. It was then heated to 180° C. and maintained there for 144 hours. During this time, mixing was obtained by spinning at 800 rpm. Starting pH was 6.5; ending pH was 6.

The crystalline product was separated from the reaction mixture by filtration, water washed and then dried at 80° C. The product crystals were analyzed and a sample of the as synthesized silicophosphoaluminate was then submitted for X-ray analysis. It was found to be a crystalline molecular sieve exhibiting diffraction lines similar to those listed in Table 2. Reaction mixture, as condition and product particulars are shown in Table 4.

TABLE 4

| Synthesis mixture composition (g) | |
|---|---|
| $H_3PO_4$ (85%) | 23.1 |
| $H_2O$ | 71.0 |
| $Al_2O_3$ | 10.0 |
| Si $(OC_2H_5)_4$ | 10.0 |
| 1-Hexanol | 60.0 |
| Organic base | |
| TEAOH (40%) | 37.0 |
| Inorganic base | |
| (ml; 5 × $10^{-2}$ M) CsOH | 2.0 |
| Conditions | |
| Nucleation time, hrs | 24 |
| Nucleation temp., °C. | 130 |
| Crystal. time, hrs. | 144 |
| Crystal. Temp., °C. | 180 |
| Spinning rate, rpm | 800 |

TABLE 4-continued

| Composition (T-atom fraction) | |
|---|---|
| Si | 19.8 |
| P | 39.6 |
| Al | 40.7 |
| Oxide composition (wt. %, as-synth.) | |
| $SiO_2$ | 14.33 |
| $P_2O_5$ | 33.90 |
| $Al_2O_3$ | 25.10 |
| N—content (wt. %) | 1.2 |
| C—content (wt. %) | 6.32 |
| Ash content (wt. %) | 85.2 |
| Ion exchange cap. (meq per g ash) | 0.80 |

EXAMPLE 5

A quantity of the crystalline silicophosphoaluminate of Example 4 was calcined at 450° C. in nitrogen for 4 hours and then X-ray analyzed. The X-ray diffraction lines are similar to those listed in Table 3.

EXAMPLE 6

A quantity of the crystalline silicophosphoaluminate of Example 1 was used to conduct the Alpha Test (described in U.S. Pat. No. 3,354,078, entirely incorporated herein by reference). The Alpha Value was 7.0

EXAMPLE 7

A quantity of the crystalline silicophosphoaluminate of Example 1 was used to conduct the constraint index test (defined in U.S. Pat. No. 4,385,195, incorporated herein by reference in its entirety). The constraint index was greater than 100 indicating a small pore structure.

EXAMPLE 8

Using a quantity of the crystalline silicophosphoaluminate of Example 2, n-hexane was converted at 1000° F. to products of which the liquid fraction contained aromatics including toluene and xylenes.

EXAMPLE 9

Using a quantity of the crystalline silicophosphoaluminate of Example 2, a 2:1 molar toluene/methanol feed was converted at 1000° F. (WHSV=0.5) into a product mixture of which the composition (feed excluded) was benzene (14%), para-xylene (24%), meta-xylene (38%), ortho-xylene (24%). The production of xylenes demonstrates the alkylation activity of the catalyst. The observation that the xylenes are in near thermodynamic equilibrium suggest aromatic isomerization activity. The presence of benzene in the products shows activity for dealkylation and/or transalkylation reactions.

EXAMPLE 10

Using a quantity of the crystalline silicophosphoaluminate of Example 1, a ethylene-toluene feed was converted at 850°-950°-F. to a mixture of all three isomers of ethyltoluene, demonstrating again the alkylation activity of the catalyst.

EXAMPLE 11

Methanol was converted (90%) at 660° F. over a quantity of the catalyst of Example 1 to a hydrocarbon product consisting of (wt.%) methane (1.2), ethane (0.7), ethylene (23.2), propane (15.3), propylene (35.5), n-butane (5.0), and C$_4$-olefins (19.1). At 950° F. and below 20% methanol conversion, the product consisted only of ethylene (69%) and propylene (31%).

Further data regarding the conversion of methanol to olefins are set for the hereinbelow.

Catalyst:
Ammonium-exchanged MCM-2 calcined at 450-500° C.
Atomic percentages Si:P:Al = 17.5:37.2:45.4 (Ex. 1).
Crystal size = ca. 1 micrometer.
Alpha value = 7 (Ex. 6).
Constraint Index greater than 100 (Ex. 7).

Reaction Conditions:
pressure = 1 atm.; Temperature = 400-500° C.
Methanol (ca. 150 torr) added to N$_2$ as vector gas.

Results:

| Sample | WHSV | T(°C.) | % CH$_2$ conv. | C2−/C3= (wt. basis) | C2 = Sel. (wt. basis) | C2 =-C4 = Sel. (wt. basis) |
|---|---|---|---|---|---|---|
| With nitrogen: | | | | | | |
| #4 | 0.4 | 400 | 68 | 1.3 | 46 | 87 |
| #5 | 0.4 | 425 | 74 | 1.7 | 53 | 88 |
| #6 | 0.4 | 450 | 69 | 2.3 | 60 | 88 |
| #7 | 0.4 | 475 | 45 | 3.7 | 64 | 82 |
| After air regeneration at 500° C. | | | | | | |
| With hydrogen (H$_2$:MeOH = 4:1) | | | | | | |
| #13 | 0.8 | 450 | 100 | 1.3 | 41 | 84 |
| #16 | 1.6 | 450 | 100 | 1.4 | 47 | 89 |
| #19 | 3.2 | 450 | 62 | 1.6 | 52 | 91 |

The MCM-2 catalyst converts methanol with ca. 90% selectivity to a mixture of C$_2$-C$_4$ olefins. Ethylene selectivity is high as seen from the ethylene/propylene ratios and the fact that it accounts for about 50 wt.% of the product hydrocarbons. Isobutane and isobutylene are not present in the products. Aging is rather rapid in the absence of hydrogen, but much less severe when hydrogen is added. The catalyst can be regenerated in air without substantial loss of catalytic activity.

The use of small pore size MCM-2 catalysts, with low acidity and good stability in air regeneration, enables the selective conversion of methanol to a C$_2$-C$_4$ olefinic mixture in the presence of hydrogen. Selectivity for ethylene is particularly high. For methanol to olefins conversion, MCM-2 silicophosphoaluminate catalysts offer an alternative to the use of aluminosilicate catalysts which may be more sensitive to air regeneration. MCM-2 appears to have a higher hydrolytic stability than its zeolitic isotype (chabazite).

Examples 12-19 which follow relate to the preparation of an MCM-2 material from an AlPO$_4$-5 starting material.

EXAMPLE 12

A synthesis reaction mixture was prepared which contained 138.3 g of H$_3$PO$_4$ (85%), 357.6 g of H$_2$O, 82.5 g of Catapal alumina, and 91.2 g of triethylamine. After stirring until the suspension was homogeneous, the mixture was poured into a 1 l steel autoclave and maintained under autogeneous pressure at 200° C. for 24 h. The product was filtered, washed, and dried at 80° C. The product crystals were analyzed to contain 48.9% Al, 51.1% P, and less than 0.03% Si, percentages atomic. A sample of the as-synthesized product was then submitted for X-ray analysis and found to be a crystalline material exhibiting the diffraction lines shown in Table 5.

TABLE 5

| D | 2TH | I/IMAX |
|---|---|---|
| 11.7535 | 7.515 | 95.99 |
| 6.8016 | 13.005 | 16.08 |
| 5.8886 | 15.033 | 28.26 |
| 4.4534 | 19.921 | 60.53 |
| 4.2109 | 21.080 | 71.59 |
| 3.9417 | 22.538 | 100.00 |
| 3.5870 | 24.800 | 5.00 |
| 3.4042 | 26.155 | 28.27 |
| 3.0617 | 29.142 | 19.01 |
| 2.9523 | 30.248 | 18.94 |
| 2.6520 | 33.771 | 6.87 |
| 2.5750 | 34.810 | 15.00 |

EXAMPLE 13

The synthesis of Example 12 was repeated resulting in a material showing the characteristic diffraction lines of Table 5 and having the composition 47.95% Al, 51.70% P, and 0.35% Si, percentages atomic.

EXAMPLE 14

A quantity of the crystalline aluminum phosphate of Example 13 was calcined at 450° C. in nitrogen for 4 h and contacted twice with a solution of 1 M NH$_4$Cl at pH=7 for 3 h at 80° C. The product was then evaluated for cationic exchange properties by the titration of gaseous ammonia released during heating from 25° to 600° C. The results of this test showed that no ammonia was released above 250° C., indicating the absence of cationic exchange sites.

EXAMPLE 15

The final product of Example 14 was submitted to the Alpha-Test. Its Alpha Value was less than 0.1.

EXAMPLE 16

A two-phase synthesis reaction mixture was prepared with the organic phase comprised of 60 g 1-hexanol and 10 g Si(OC$_2$H$_5$)$_4$, and the aqueous phase comprised of 71 g H$_2$O, 24 g of the product of Example 12 calcined at 450° C. in nitrogen for 4 h, and 37 g of tetraethylammonium hydroxide (40%). After stirring until the mixture appeared homogeneous, the mixture was transferred to a 0.3 l steel autoclave and heated to and maintained at 180° C. for 7 days. The starting and final pH was between 6 and 8. The crystalline product was separated from the reaction mixture by filtration, water washed, and then dried at 80° C. The product crystals were analyzed to contain 41.1% Al, 42.8% P, and 16.1% Si, percentages atomic. The Al/P ratio was 0.96. A sample of the as-synthesized product silicophosphoaluminate was then submitted for X-ray analysis and found to be a crystalline structure exhibiting the diffraction lines shown in Table 6 which are characteristic for MCM-2.

TABLE 6

| D | 2TH | I/IMAX |
|---|---|---|
| 9.2777 | 9.525 | 100.00 |
| 6.8832 | 12.851 | 17.26 |
| 6.2774 | 14.097 | 15.85 |
| 5.5276 | 16.021 | 80.96 |
| 4.9185 | 18.020 | 15.09 |
| 4.6701 | 18.987 | 2.66 |
| 4.3119 | 20.581 | 98.58 |
| 3.9922 | 22.249 | 4.58 |
| 3.8475 | 23.098 | 4.35 |
| 3.5163 | 25.308 | 19.04 |
| 3.4447 | 25.843 | 19.47 |
| 3.0224 | 29.530 | 2.98 |
| 2.9248 | 30.539 | 35.79 |
| 2.8587 | 31.264 | 35.38 |
| 2.6051 | 34.396 | 6.06 |

EXAMPLE 17

The synthesis of Example 16 was repeated using the calcined product of Example 13 as a source of aluminum and phosphorus. The crystalline product was separated from the crystallization mixture by filtration, water washed, and dried at 80° C. The product crystals were analyzed to contain 44.9% Al, 41.6% P, and 13.5% Si, percentages atomic. The Al/P ratio was 1.08. A sample of the as-synthesized product silicophosphoaluminate was then submitted for X-ray analysis and found to be a crystalline structure exhibiting the diffraction lines shown in Table 7 which are characteristic for MCM-2.

TABLE 7

| D | 2TH | I/IMAX |
|---|---|---|
| 9.2698 | 9.533 | 100.00 |
| 6.8803 | 12.856 | 15.13 |
| 6.2784 | 14.094 | 14.22 |
| 5.5226 | 16.035 | 77.00 |
| 4.9233 | 18.002 | 12.70 |
| 4.6787 | 18.952 | 5.80 |
| 4.3088 | 20.596 | 96.57 |
| 3.9959 | 22.228 | 5.61 |
| 3.8416 | 23.133 | 4.54 |
| 3.5131 | 25.331 | 29.89 |

TABLE 7-continued

| D | 2TH | I/IMAX |
|---|---|---|
| 3.4435 | 25.852 | 21.11 |
| 3.3408 | 26.661 | 15.04 |
| 3.1505 | 28.304 | 6.42 |
| 3.0239 | 29.515 | 4.06 |
| 2.9234 | 30.555 | 39.38 |
| 2.8602 | 31.247 | 38.68 |
| 2.6071 | 34.369 | 6.26 |

EXAMPLE 18

A quantity of the crystalline product of Example 17 was calcined at 450° C. in nitrogen for 4 h and contacted twice with a solution of 1 M NH$_4$Cl at pH=7 for 3 h at 80° C. The product was then evaluated for cationic exchange properties by the titration of gaseous ammonia released during heating from 25° to 600° C. The results show the release of two types of ammonia. Low temperature ammonia released up to 250° C. amounted to 1.45 meq/g whereas high temperature ammonia, corresponding to cationic sites, was 1.14 meq/g. The maximum rate of desorption for the high temperature ammonia was observed at 375° C.

EXAMPLE 19

The final product of Example 18 was submitted to the Alpha-Test. Its Alpha Value was 4.8, indicating a 48 fold or even higher increase in catalytic activity relative to the product material of Example 13.

It will be understood that the silicon, phosphorus and aluminum portions of the reactants discussed hereinabove may possibly be replaced in whole or in part, with functionally equivalent elements. For example, in the field of crystalline aluminosilicate zeolites it has been found that the silicon portion thereof may be replaced with, e.g., germanium, and the aluminum portion thereof may be replaced with iron, chromium, vanadium, molybdenum, arsenic, antimony, manganese, gallium or boron.

What is claimed is:

1. A method for preparing an MCM-2 material, said method comprising the steps of:
 (i) providing a synthesis mixture comprising a liquid organic phase and a liquid aqueous phase, said organic phase comprising an organic solvent immiscible with water and a silicon source soluble in said solvent, said aqueous phase comprising dissolved or partially dissolved AlPO$_4$-5 crystalline aluminum phosphate, said synthesis mixture further comprising a tetraethylammonium directing agent;
 (ii) maintaining said reaction mixture under sufficient crystallization conditions until crystals of said MCM-2 are formed; and
 (iii) recovering said MCM-2.

2. A method according to claim 1, wherein the organic solvent immiscible with water is a C$_5$–C$_{10}$ alcohol.

* * * * *

UNITED STATES PATENT AND TRADEMARK OFFICE
CERTIFICATE OF CORRECTION

PATENT NO. : 4,647,442

DATED : March 3, 1987

INVENTOR(S) : E. G. Derouane & R. von Ballmoos

It is certified that error appears in the above-identified patent and that said Letters Patent is hereby corrected as shown below:

Col. 13, line 14, insert --Total-- before "pressure"

Signed and Sealed this

Eighteenth Day of August, 1987

*Attest:*

DONALD J. QUIGG

*Attesting Officer*      *Commissioner of Patents and Trademarks*